US006194137B1

(12) United States Patent
Khirabadi et al.

(10) Patent No.: US 6,194,137 B1
(45) Date of Patent: Feb. 27, 2001

(54) METHOD OF CRYOPRESERVATION OF BLOOD VESSELS BY VITRIFICATION

(75) Inventors: Bijan S. Khirabadi, Rockville, MD (US); Ying C. Song, Mt. Pleasant; Kelvin G. M. Brockbank, Charleston, both of SC (US)

(73) Assignee: Organ Recovery Systems, Inc., Chicago, IL (US)

( * ) Notice: Subject to any disclaimer, the term of this patent is extended or adjusted under 35 U.S.C. 154(b) by 0 days.

(21) Appl. No.: 09/289,977

(22) Filed: Apr. 13, 1999

(51) Int. Cl.$^7$ ..................................................... A01N 1/02

(52) U.S. Cl. .................................................... 435/1.3

(58) Field of Search ............................................. 435/1.3

(56) References Cited

U.S. PATENT DOCUMENTS

| | | |
|---|---|---|
| 4,494,385 | 1/1985 | Kuraoka et al. . |
| 4,559,298 | 12/1985 | Fahy . |
| 5,122,110 | 6/1992 | McNally et al. . |
| 5,145,769 | 9/1992 | McNally et al. . |
| 5,149,621 | 9/1992 | McNally et al. . |
| 5,158,867 | 10/1992 | McNally et al. . |
| 5,217,860 | 6/1993 | Fahy et al. . |
| 5,472,876 | 12/1995 | Fahy . |
| 5,518,878 | 5/1996 | Wilkins et al. . |
| 5,723,282 | 3/1998 | Fahy et al. . |
| 5,821,045 | 10/1998 | Fahy et al. . |
| 5,856,081 | 1/1999 | Fahy . |

OTHER PUBLICATIONS

Armitage, "Survival of Corneal Endothelium following Exposure to a Vitrification Solution," Cryobiology, vol. 26, 1989, pp. 318–327.

Bourne et al., "Human Corneal Studies with a Vitrification Solution Containing Dimethyl Sulfoxide, Formamide, and 1,2–Propanediol," Cryobiology, vol. 31, No. 6, 1994, pp. 522–530.

Dent et al., "Cryopreservation of Vein Grafts," Surgical Forum, vol. 25, pp. 241–243.

Brockbank et al., "Cryopreserved Vein Transplantation," Journal of Cardiac Surgery, vol. 7, No. 2, pp. 170–176, 1992.

Else Müller–Schweinitzer, "Cryopreservation: a useful technique for storing tissues for pharmacological investigations," Reprinted from Trends in Pharmacological Sciences; vol. 9, No. 6, pp. 221–223; Jun. 1988.

Weber et al., "Viable Vein Graft Preservation," Journal of Surgical Research 18, pp. 247–255, 1975.

Bishop et al., "A morphological assessment of vein allografts preserved in glycerol and used for arterial replacement," Journal of Cardiovascular Surgery 28, pp. 491–497, 1987.

Barner et al., "Fresh and Frozen Homologous Venous Grafts for Arterial Repair," Angiology 17, pp. 389–401, 1966.

Sitzmann et al., "Dimethylsulfoxide–treated, cryopreserved venous allografts in the arterial and venous systems," Surgery, vol. 95, No. 2, pp. 154–159, 1984.

Song et al., "Cryopreservation of the Common Carotid Artery of the Rabbit: Optimization of Dimethyl Sulfoxide Concentration and Cooling Rate," Cryobiology 32, pp 405–421, 1995.

Wusteman et al., "The Effect of Cooling Rate and Temperature on the Toxicity of Ethylene Glycol in the Rabbit Internal Carotid Artery," Cryobiology 33, pp. 423–429, 1996.

Narayanan et al., "Successful Cryopreservation of Microvenous Allografts," Journal of Investigative Surgery, vol. 5, pp. 155–160, 1992.

Ku et al., "Human Coronary Vascular Smooth Muscle and Endothelium–Dependent Responses after Storage at −75°C," Cryobiology 29, pp. 199–209, 1992.

Müller–Schweinitzer et al., "Sucrose promotes the functional activity of blood vessels after cryopreservation in DMSO–containing fetal calf serum," Naunyn–Schmiedeberg's Archives of Pharmacology, pp. 1–4, 1992.

Müller–Schweinitzer et al., "Functional recovery of human mesenteric and coronary arteries after cryopreservation at −196°C in a serum–free medium," Journal of Vascular Surgery, vol. 25, No. 4, pp. 743–749, 1997.

Fahy et al., G. M., "Vitrification as an Approach to Cryopreservation," *Cryobiology* 21, 407–426 (1984).

Chen et al., X. H., "Vitrification of Multicomponent Solutions by Cooling to Cryogenic Temperatures," *Cryogenics* 1990 vol. 30 Sept. Supplement, pp. 541–545.

Fahy et al. G. M., "Some Emerging Principles Underlying the Physical Properties, Biological Actions, and Utility of Vitrification Solutions," *Cryobiology* 24, 196–213 (1987).

(List continued on next page.)

*Primary Examiner*—Sandra E. Saucier
(74) *Attorney, Agent, or Firm*—Oliff & Berridge, PLC (57) ABSTRACT

A method for vitrification of a blood vessel includes immersing the blood vessel in increasing concentrations of cryoprotectant solution at a temperature greater than −15° C. to a cryoprotectant concentration sufficient for vitrification; cooling the blood vessel at an average rate of from 30–60° C. per minute to a temperature between −80° C. and the glass transition temperature; and further cooling the blood vessel at an average rate less than 10° C. per minute to a temperature below the glass transition temperature to vitrify the blood vessel. After the vitrified blood vessel has been stored, the blood vessel may be removed from vitrification by warming the blood vessel at an average rate of from 20–40° C. per minute to a temperature between −80° C. and the glass transition temperature; further warming the blood vessel at a rate of from 200–300° C. per minute to a temperature above −15° C.; and reducing the concentration of the cryoprotectant. Blood vessels treated in this manner exhibit near normal smooth muscle function, normal graft patency rates, and reduced levels of intimal hyperplasia.

15 Claims, 6 Drawing Sheets

OTHER PUBLICATIONS

Ren et al., H. S., "The Crystallization Kinetics and the Critical Cooling Rates for Vitrification of Cryoprotective Solution," *Cryogenics* 1990, vol. 30, Sep. Supplement, pp. 536–540.

Guttman et al., Frank M., "Variation of Cooling Rate and Concentration of Dimethyl Sulfoxide on Rabbit Kidney Function," *Cryobiology*, 23, 495–499 (1986).

Jacobsen et al., I.A., "Effect of Cooling and Warming Rate on Glycerolized Rabbit Kidneys," *Cryobiology* 19:668 (1982).

Fresh 2 Week Grafts      Vitrified 4 Week Grafts

A     Graft at implantation     B

C     Graft after perfusion     D
fixation and removal E     Graft dissection     F

METHOD OF CRYOPRESERVATION OF BLOOD VESSELS BY VITRIFICATION

BACKGROUND OF THE INVENTION

The U.S. Government has a paid-up license in this invention and the right in limited circumstances to require the patent owner to license others on reasonable terms as provided by the terms of cooperative agreement No. 70NANB7H3071 awarded by NIST.

In the present era of arterial replacement, at least 345,000–485,000 autologous coronary grafts (either arteries or veins) and over 200,000 autogenous vein grafts into peripheral arteries are performed each year. Report of a working party of the British Cardiac Society: Coronary Angioplasty in the United Kingdom. *Br Heart J*. 66:325–331, 1991; Heart and Stroke Facts: Statistical Supplement, American Heart Association, 1996; and Callow A. D. "Historical overview of experimental and clinical development of vascular grafts," In: Biologic and Synthetic Vascular Prosthesis, Stanley J (Ed), Grune and Stratton, New York, 11, 1983. A recent marketing report indicated that at least 300,000 coronary artery bypass procedures are performed annually in the United States involving in excess of 1 million vascular grafts. World Cell Therapy Markets, Frost & Sullivan, 5413–43 Revision #1, ISBN 0-7889-0693-3, 1997.

Many of these patients do not have autologous veins suitable for grafts due to pre-existing vascular disease, vein stripping or use in prior vascular procedures. It has been estimated that as many as 30% of the patients who require arterial bypass procedures will have saphenous veins unsuitable for use in vascular reconstruction. Edwards W. S., Holdefer W. F., Motashemi, M., "The importance of proper caliber of lumen in femoral popliteal artery reconstruction," *Surg Gynecol Obstet*. 122:37, 1966. More recently it has been demonstrated that 2–5% of saphenous veins considered for bypass procedures were unusable on the basis of gross pathology and that up to 12% were subsequently classified as diseased. These "diseased" veins had patency rates less than half that of non-diseased veins. Panetta T. F., Marin M. L., Veith F. J., et al., "Unsuspected pre-existing saphenous vein disease: an unrecognized cause of vein bypass failure," *J Vasc Surg*. 15:102–112, 1992. However, we estimate that if all arterial grafts and alternative veins are utilized according to current surgical practice, the maximum number of potential allograft recipients is probably closer to 10%.

Vitrified arterial grafts may also have a market as a scaffold for the seeding and adhesion of autologous endothelial cells or genetically modified endothelial cells. Prosthetic grafts are currently employed for large diameter (greater than 6mm internal diameter) non-coronary applications. Between 1985 and 1990, approximately 1,200 allogeneic vein segments were employed for arterial bypass. Brockbank K. G. M., McNally R. T., Walsh K. A., "Cryopreserved vein transplantation," *J Cardiac Surg*. 7:170–176, 1992. The demand for allogeneic veins is growing despite the well documented immune response to these grafts and the low clinical patency rates. In 1991 alone, at least 1,400 allograft saphenous vein segments were transplanted. McNally R. T., Walsh K., Richardson W., "Early clinical evaluation of cryopreserved allograft vein," Proceedings of the 29th meeting of the Society for Cryobiology, *Cryobio.*, Abstract #4, 1992. Conservatively, the market potential for vitrified vascular grafts may be 50,000 units per year, or 10% of all vascular grafting procedures in the United States.

Blood vessels are also a ubiquitous component of vascularized tissues and organs, both human and animal, which may one day be successfully stored by vitrification for transplantation. Providing that significant immunological issues can be overcome, animal-derived grafts may, one day, provide an unlimited supply of blood vessels and vascularized tissues and organs that could be stored in a vitrified state prior to transplantation.

Low temperature preservation of biological tissues and organs, i.e., cryopreservation, has been the subject of much research effort. Cryopreservation can be approached by freezing or by vitrification. If the organ or tissue is frozen, ice crystals may form within the organ or tissue that may mechanically disrupt its structure and thus damage its ability to function correctly when it is transplanted into a recipient. Organized tissues and organs are particularly susceptible to mechanical damage from ice crystals formed during freezing.

Vitrification, by contrast, means solidification, as in a glass, without ice crystal formation. The principles of vitrification are well-known. Generally, the lowest temperature a solution can possibly supercool to without freezing is the homogeneous nucleation temperature $T_h$, at which temperature ice crystals nucleate and grow, and a crystalline solid is formed from the solution. Vitrification solutions have a glass transition temperature $T_g$, at which temperature the solute vitrifies, or becomes a non-crystalline solid. Owing to the kinetics of nucleation and crystal growth, it is effectively impossible for water molecules to align for crystal formation at temperatures much below $T_g$. In addition, on cooling most dilute aqueous solutions to the glass transition temperature, $T_h$ is encountered before $T_g$, and ice nucleation occurs, which makes it impossible to vitrify the solution. In order to make such solutions useful in the preservation of biological materials by vitrification, it is therefore necessary to change the properties of the solution so that vitrification occurs instead of ice crystal nucleation and growth. It is also important that all viability and tissue function be maintained by the entire vitrification process.

While it is generally known that high hydrostatic pressures raise $T_g$ and lower $T_h$, vitrification of most dilute solutions by the application of pressure is often impossible or impractical. In particular, for many solutions vitrifiable by the application of pressure, the required pressures cause unacceptably severe injury to unprotected biomaterials during vitrification thereof While it is also known that many solutes, such as commonly employed cryoprotectants like dimethyl sulfoxide (DMSO), raise $T_g$ and lower $T_h$, solution concentrations of DMSO or similar solutes high enough to permit vitrification typically approach the eutectic concentration and are generally toxic to biological materials.

One type of damage caused by cryoprotectants is osmotic damage. Cryobiologists learned of the osmotic effects of cryoprotectants in the 1950's and of the necessity of controlling these effects so as to prevent damage during the addition and removal of cryoprotectants to isolated cells and tissues. Similar lessons were learned when cryobiologists moved on to studies of whole organ perfusion with cryoprotectants. Attention to the principles of osmosis were essential to induce tolerance to cryoprotectant addition to organs.

Despite efforts to control the deleterious osmotic effects of cryoprotectants, limits of tolerance to cryoprotectants are still observed. There appear to be genuine, inherent toxic effects of cryoprotectants that are independent of the transient osmotic effects of these chemical agents.

Studies by the present inventors and others have examined methods of controlling non-osmotic, inherent toxicity of cryoprotectant agents. The results indicate that several techniques can be effective alone and in combination. These include (a) the use of specific combinations of cryoprotectant whose effects cancel out each other's toxicities; (b) exposure to cryoprotectants in vehicle solutions that are optimized for those particular cryoprotectants; (c) the use of non-penetrating agents that can substitute for a portion of the penetrating agent otherwise needed, thus sparing the cellular interior from exposure to additional intracellular agents; and (d) minimizing the time spent within the concentration range of rapid time-dependent toxicity.

Some of these techniques are in potential conflict with need to control osmotic forces. For example, reduced temperatures also reduce the influx and efflux rate of cryoprotectants, thereby prolonging and intensifying their osmotic effects. Similarly, minimizing exposure time to cryoprotectants maximizes their potential osmotic effects. Thus, there must be a balance reached between the control of osmotic damage and the control of toxicity. Means for obtaining this balance are described in U.S. Pat. No. 5,723,282 to Fahy et al. However, this patent does not describe a particular method to be used for blood vessels. In addition, this patent does not discuss any protocols for cooling or warming the organ or tissue.

SUMMARY OF THE INVENTION

The present invention is directed to a method for vitrification of a blood vessel. The method comprises immersing the blood vessel in increasing concentrations of cryoprotectant solution at a temperature greater than −5° C. to a cryoprotectant concentration sufficient for vitrification; rapidly cooling the blood vessel to a temperature between −80° C. and the glass transition temperature ($T_g$); and further cooling the blood vessel from a temperature above the glass transition temperature to a temperature below the glass transition temperature to vitrify the blood vessel.

The present invention is also directed to a method for removing a blood vessel from vitrification in a cryoprotectant solution. The method comprises slowly warming a vitrified blood vessel in the cryoprotectant solution to a temperature between −80° C. and the glass transition temperature; rapidly warming the blood vessel in the cryoprotectant solution to a temperature above −75° C.; and reducing the concentration of the cryoprotectant by immersing the blood vessel in decreasing concentrations of cryoprotectant.

The present invention is also directed to a method for treating blood vessels such that smooth muscle functions and graft patency rate are maintained and intimal hyperplasia is reduced relative to fresh untreated controls. In particular, the present invention is directed to a method in which at least 70%, preferably at least 80%, of smooth muscle function and graft patency rate are maintained relative to fresh untreated controls.

DETAILED DESCRIPTION OF PREFERRED EMBODIMENTS

The present invention is directed to a method for vitrification of a blood vessel in a cryoprotectant solution and for subsequently removing the blood vessel from vitrification. "Blood vessel" is used herein to refer to any biological tube conveying blood. Thus, the phrase refers to an artery, capillary, vein, sinus or engineered construct.

As used herein, the term "vitrification" refers to solidification without ice crystal formation. As used herein, a tissue is vitrified when it reaches the glass transition temperature (Tg).

As used herein, the "glass transition temperature" refers to the glass transition temperature of a solution under the conditions at which the process is being conducted. In general, the process of the present invention is conducted at physiological pressures. However, higher pressures can be used as long as the blood vessel is not significantly damaged thereby.

As used herein, "physiological pressures" refer to pressures that blood vessels undergo during normal function. The term "physiological pressures" thus includes normal atmospheric conditions, as well as the higher pressures blood vessels undergo under diastolic and systolic conditions.

As used herein, the term "perfusion" means the flowing of a fluid through the blood vessel. Techniques for perfusing organs and tissues are discussed in, for example, U.S. Pat. No. 5,723,282 to Fahy et al., which is incorporated herein in its entirety.

As used herein, the term "cryoprotectant" means a chemical that inhibits ice crystal formation in a tissue or organ when the tissue or organ is cooled to subzero temperatures and results in an increase in viability after warming, in comparison to the effect of cooling without cryoprotectant.

As used herein, "approximate osmotic equilibration" means that there is no more than a 10% difference between the intracellular and extracellular solute concentrations. A difference of no more than 10% means, for example, that, if the extracellular concentration is 4M, the intracellular solute concentration is between 3.6 and 4.4M. Preferably, there is no more than a 5% difference between the intracellular and extracellular concentrations.

In the method of the present invention, the blood vessel is immersed in increasing concentrations of cryoprotectant solution at a temperature greater than −5° C. The temperature is preferably between 0° C. and 15° C., more preferably between 0° C. and 10° C. Preferably, the blood vessel is also perfused with the increasing concentrations of cryoprotectant.

The increase in concentration is preferably conducted in a step-wise manner. That is, cryoprotectant is added to the extracellular solution to achieve a particular concentration of cryoprotectant. After this concentration level is obtained, the concentration of the solution is then substantially maintained for a period of time. In particular, the concentration level is generally maintained for a sufficient time to permit approximate osmotic equilibration of the blood vessel in the solution. To obtain approximate osmotic equilibration, the concentration level is generally maintained for at least 10 minutes. In a preferred embodiment, the concentration level is maintained for at least 15 minutes. This process is repeated as many times as necessary, with the final concentration being sufficient for vitrification at physiological pressures, particularly under normal atmospheric conditions. In addition, the blood vessel is generally maintained at each concentration level for no more than an hour, preferably for no more than 30 minutes.

In general, the blood vessel is first immersed in a cryoprotectant-free solution. The blood vessel may also be perfused with the cryoprotectant-free solution. This cryoprotectant-free solution can be any type of solution that maintains cellular integrity under in vitro conditions as typified by synthetic physical buffers at normal temperatures, and organ preservation solutions at hypothermic temperatures. Most typically, the initial cryoprotectant-free solution will be the same as the vehicle solution used to add and remove cryoprotectants in the blood vessel. For example, the cryoprotectant-free solution can be a Euro-Collins solution, which is an aqueous solution described in Table 1 below.

TABLE 1

Euro-Collins*

| Compound | mM | g/l |
|---|---|---|
| Dextrose | 194 | 34.96 |
| KH$_2$PO$_4$ | 15 | 2.06 |
| K$_2$HPO$_4$ | 42 | 7.40 |
| KCl | 15 | 1.12 |
| NaHCO$_3$ | 10 | 0.84 |

*pH = 7.4
*milliosmolality = 350–365 milliosmolal

Other suitable aqueous solutions are discussed in Tables 2 and 3 below.

TABLE 2

Modified RPS-2

| Compound | mM | g/l |
|---|---|---|
| Dextrose | 180 | 32.43 |
| K$_2$HPO$_4$ | 7.2 | 1.25 |
| KCl | 28.2 | 2.11 |
| NaHCO$_3$ | 10 | 0.84 |
| Glutathione | 5 | 1.53 |
| Adenine HCl | 1 | 0.17 |
| CaCl$_2$ | 1 | 0.111 |
| MgCl$_2$ | 2 | 0.407 |

(Note: RPS-2 ™ solution is modified RPS-2 without CaCl$_2$ and also without MgCl$_2$)

TABLE 3

| Modified UW Solution #1 | | | Modified UW Solution #2 | | |
|---|---|---|---|---|---|
| Compound | mM | g/l | Compound | mM | g/l |
| NaH$_2$PO$_4$.H$_2$O | 25 | 3.45 | NaH$_2$PO$_4$.H$_2$O | 25 | 3.45 |
| K glutonate | 100 | 23.42 | K gluconate | 100 | 23.42 |
| Mg glutonate | 1 | 0.21 | Mg gluconate | 1 | 0.21 |
| glucose | 5 | 0.90 | glucose | 15 | 2.70 |
| glutathione | 3 | 0.92 | glutathione | 3 | 0.92 |

TABLE 3-continued

| Modified UW Solution #1 | | | Modified UW Solution #2 | | |
|---|---|---|---|---|---|
| Compound | mM | g/l | Compound | mM | g/l |
| adenosine | 5 | 1.34 | adenosine | 5 | 1.34 |
| HEPES | 10 | 2.38 | HEPES | 10 | 2.38 |
| adenine (hydrochloride) | 1 | 0.17 | adenine (hydrochloride) | 1 | 0.17 |
| ribose | 1 | 0.15 | ribose | 1 | 0.15 |
| CaCl$_2$ | 0.05 | 0.0056 | CaCl$_2$ | 0.05 | 0.0056 |
| HES(g) | — | 50 | — | — | — |

(Note: Modified UW Solution #2 does not contain HES but contains more glucose than modified UW Solution #1)

After being immersed in a cryoprotectant-free solution, the blood vessel is immersed in a solution containing cryoprotectant. A cryoprotectant concentration sufficient for vitrification generally contains from 6.0 to 9.5M cryoprotectant, preferably from 7 to 9M cryoprotectant, more preferably from 8 to 9M cryoprotectant. The cryoprotectant solution may contain any combination of cryoprotectants sufficient for vitrification. Cryoprotectants include, but are not limited to, dimethyl sulfoxide, formamide, 1,2-propanediol, 2,3-butanediol, glycerol, ethylene glycol, n-dimethyl formamide and 1,3-propanediol.

Impermeable cryoprotectant agents such as polyvinylpyrrolidone or hydroxyethyl starch may be more effective at protecting biological systems cooled at rapid rates. Such agents are often large macromolecules, which effect the properties of the solution to a greater extent than would be expected from their osmotic pressure. Some of these non-permeating cryoprotectant agents have direct protective effects on the cell membrane. However, the primary mechanism of action appears to be the induction of extracellular glass formation. When such cryoprotectants are used in extremely high concentrations, ice formation may be eliminated entirely during cooling to and warming from cryogenic temperatures. Impermeable chemicals with demonstrated cryoprotective activity include agarose, dextrans, glucose, hydroxyethylstarch, inositol, lactose, methyl glucose, polyvinylpyrrolidone, sorbitol, sucrose and urea.

In a particular embodiment of the present invention, the cryoprotectant solution contains dimethyl sulfoxide, formamide, and 1,2-propanediol. For example, the cryoprotectant solution may be a solution called VS55. VS55 is a solution containing 24.2% w/v (3.1M) dimethyl sulfoxide, 16.8% w/v (2.2M) 1,2-propanediol, and 14.0% w/v (3.1M) formamide. Thus, the solution contains about 55% w/v cryoprotectant or 8.4M cryoprotectant. The amount of dimethyl sulfoxide may be varied from 20 to 30% w/v. Similarly, the amount of 1,2-propanediol and formamide may each be varied from about 10 to 20% w/v. However, the total amount of cryoprotectant in the full strength solution should be between 45% w/v to 60% w/v, preferably from about 50% w/v to 55% w/v.

In addition, in further preferred embodiments of the invention, 1,2-propanediol may be replaced by similar concentrations of 2,3-butanediol. Similarly, dimethyl sulfoxide may be replaced by similar concentrations of glycerol or ethylene glycol or combinations of thereof.

The vehicle for the cryoprotectant solution may be any type of solution that maintains cellular integrity under in vitro conditions. In particular, the vehicle generally comprises slowly penetrating solutes. In VS55, the vehicle solution is a Euro-Collins solution containing 10 mM HEPES. HEPES is included as a buffer and may be included in any effective amount. In addition, other buffers, as well as no buffer, may be used. Alternative vehicles include, but are not limited to, the solutions discussed in Tables 2 and 3 above.

The final concentration of the perfusion solution is sufficient to vitrify the blood vessel. However, as discussed above, the concentration of the solution is gradually increased to achieve this level, preferably in a step-wise manner. In particular, cryoprotectant is added to achieve a particular plateau, which is maintained for a sufficient time to achieve approximate osmotic equilibration, in particular for at least 10 minutes and preferably for about 15 minutes. Then, further cryoprotectant is added to increase the cryoprotectant concentration, which may or may not be a level sufficient for vitrification. If not, after maintaining the concentration for sufficient time to achieve approximate osmotic equilibration, further cryoprotectant is added in one or more steps to achieve a concentration sufficient for vitrification.

In a preferred embodiment of the invention, there are four cryoprotectant concentration plateaus before reaching the concentration sufficient for vitrification. In this preferred embodiment, there are thus six steps, the first step using a cryoprotectant-free solution, which is followed by four increasing cryoprotectant concentration plateaus and then a cryoprotectant concentration sufficient for vitrification. In a particularly preferred six step embodiment, in step 1, no cryoprotectant is used; in step 2, 5 to 20%, preferably 10 to 15%, of the final cryoprotectant concentration is used; in step 3, 15 to 35%, preferably 20 to 30%, of the final cryoprotectant concentration is used; in step 4, 40 to 60%, preferably 45 to 55%, of the final cryoprotectant concentration is used; in step 5, 65 to 85%, preferably 70 to 80%, of the final cryoprotectant concentration is used; and in step 6, the final cryoprotectant concentration, which is sufficient for vitrification, is used. Each cryoprotectant concentration step is maintained for a sufficient time to achieve approximate osmotic equilibration. In a further preferred embodiment, the blood vessel is perfused with the solution at each step.

After the blood vessel has been immersed in a solution containing a concentration of cryoprotectant sufficient for vitrification, the blood vessel, which is maintained in a solution containing a concentration of cryoprotectant sufficient for vitrification, is rapidly cooled to a temperature between −80° C. and the glass transition temperature. The rapid cooling rate is generally at least 25° C. per minute. The average cooling rate during this step is preferably from 30–60° C. per minute, more preferably from 35–50° C. per minute, and even more preferably from 40–45° C. per minute. The temperature to which the blood vessel is cooled during this rapid cooling process is preferably between −90 and −110° C., more preferably between −95 and −105° C.

After the blood vessel undergoes this rapid cooling process, the blood vessel then undergoes a slow cooling process in which the blood vessel is cooled at an average rate less than 10° C. per minute from a temperature above the glass transition temperature to a temperature below the glass transition temperature to vitrify the blood vessel. The cooling process is preferably conducted at an average rate less than 5° C. per minute. Preferably, the rate of cooling during this entire step does not increase above 10° C. per minute, more preferably the rate of cooling does not increase above 5° C. per minute. The glass transition temperature is generally about −120° C. to −135° C. under normal atmospheric conditions. The blood vessel can then be stored for long period of time at a temperature below the glass transition temperature.

In an embodiment of the invention, the slow cooling rate is achieved by changing the environment in which the container containing the solution is placed. In a particular embodiment, the rapid cooling rate is achieved by placing the container in a liquid, such as 2-methylbutane, that has been pre-cooled to a temperature below −100° C., preferably near or below the glass transition temperature of the solution to be cooled. Then, to achieve the slow cooling rate, the container is removed from the liquid and cooled in a gaseous environment at a temperature below the glass transition temperature.

The present invention is also directed to a method for removing a blood vessel from vitrification in a cryoprotectant solution. The method comprises slowly warming a vitrified blood vessel in the cryoprotectant solution to a temperature between −80° C. and the glass transition temperature. The slow warming rate is generally below 50° C. per minute. In addition, the average warming rate during this stage is generally from 20–40° C. per minute, preferably from 25–35° C. per minute. In addition, the temperature to which the vitrified blood vessel is slowly warmed is preferably between −90 and −110° C., more preferably between −95 and −105° C.

After the blood vessel has undergone this slow warming process, the blood vessel is then rapidly warmed to a temperature above −75° C. The temperature should be sufficiently high that the solution is suffiienctly fluid that the blood vessel can be removed therefrom. The rapid warming process is generally conducted at a rate above 80° C. per minute, preferably above 100° C. per minute. The average warming rate during this step is preferably from 200–300° C. per minute, more preferably from 215–250° C. per minute. The blood vessel is preferably warmed in this process to a temperature between −75° C. and −55° C. However, in a further embodiment of the invention, the blood vessel is warmed in this step to a temperature above −5° C., preferably between −5° C. and +5° C.

In an embodiment of the invention, the rapid warming rate is achieved by changing the environment in which the container containing the solution is placed. In a particular embodiment, the slow warming rate is achieved by placing the container in a gaseous environment at a temperature above the temperature at which the blood vessel has been stored. Then, to achieve the rapid warming rate, the container is placed in a liquid, such as an aqueous solution of, for example, dimethyl sulfoxide (DMSO), at a temperature above −75° C., preferably above 0° C., and more preferably at normal atmospheric temperatures.

After the blood vessel has been warmed to a temperature above −65° C., the concentration of the cryoprotectant in the solution is gradually reduced. Preferably, the cryoprotectant concentration is reduced in a step-wise manner. In an embodiment of the invention, decreasing cryoprotectant solutions are achieved by immersing the blood vessels in a series of decreasing cryoprotectant concentration solutions to facilitate elution of cryoprotectants from the blood vessel. The blood vessel may also be perfused with the solutions. The solutions are generally at a temperature above −15° C., preferably between −15 and +15° C., more preferably between 0° C. and 10° C.

The cryoprotectant concentration is preferably reduced to achieve a particular plateau, which is maintained for a sufficient time to achieve approximate osmotic equilibration, in particular for at least 10 minutes and preferably for about 15 minutes. Then, the cryoprotectant concentration is further reduced, which may or may not provide for a cryoprotectant-free solution. If not, after maintaining the concentration for sufficient time to achieve approximate osmotic equilibration, the cryoprotectant concentration is again further reduced in one or more steps to eventually provide a cryoprotectant-free solution. In addition, the blood vessel is generally immersed in each solution for no longer than an hour, preferably no longer than 30 minutes.

To decrease the cryoprotectant concentration, the cryoprotectant solution may be mixed with a solution of a type similar to the cryoprotectant-free solution utilized in adding cryoprotectant to the blood vessel. The solution preferably comprises at least one osmotic buffering agent.

As used herein, "osmotic buffering agent" means a low or high molecular weight non-penetrating extracellular solute that counteracts the osmotic effects of the greater intracellular than extracellular concentrations of cryoprotectant during the cryoprotectant efflux process.

As used herein "non-penetrating" means that the great majority of molecules of the chemical do not penetrate into the cells of the blood vessel but instead remain in the extracellular fluid of the tissue.

As used herein, "low molecular weight osmotic buffering agents" have a relative molecular mass of 1,000 daltons or less. Low molecular weight osmotic buffering agents include, but are not limited to, maltose, potassium and sodium fructose 1,6-diphosphate, potassium and sodium lactobionate, potassium and sodium glycerophosphate, maltopentose, stachyose, mannitol, sucrose, glucose, maltotriose, sodium and potassium gluconate, sodium and potassium glucose 6-phosphate, and raffinose. In a preferred embodiment, the low molecular weight osmotic buffering agent is at least one of mannitol, sucrose and raffinose.

As used herein, "high molecular weight osmotic buffering agents" generally have a relative molecular mass of from greater than 1,000 to 500,000 daltons. High molecular weight osmotic buffering agents include, but are not limited to, hydroxyethyl starch (HES), polyvinylpyrrolidone (PVP), potassium raffinose undecaacetate (>1,000 daltons) and Ficoll (greater than 1,000 to 100,000 daltons). In a preferred embodiment, the high molecular weight osmotic buffering agent is HES, more preferably having a molecular weight of about 450,000.

The cryoprotectant-free solution preferably contains less than about 500 mM of an osmotic buffering agent, more preferably from about 200 to 400 mM osmotic buffering agent. As the osmotic buffering agent, preferably a low molecular weight osmotic buffering agent is used. Most preferably, the low molecular weight osmotic buffering agent is mannitol.

In a particularly preferred embodiment, the cryoprotectant is removed in seven steps. In the preferred embodiment, in step 1, the cryoprotectant concentration is 40 to 60%, preferably 45 to 55%, of the cryoprotectant concentration used for vitrification; in a step 2, the cryoprotectant concentration is 30 to 45%, preferably 35 to 40%, of the cryoprotectant concentration used for vitrification; in step 3, the cryoprotectant concentration is 15 to 35%, preferably 20 to 30%, of the cryoprotectant concentration used for vitrification; in step 4, the cryoprotectant concentration is 5 to 20%, preferably 10 to 15%, of the cryoprotectant concentration used for vitrification; and in step 5, the cryoprotectant concentration is 2.5 to 10%, preferably 5 to 7.5%, of the cryoprotectant concentration used for vitrification. In these steps, the remainder of the solution is a cryoprotectant-free solution containing osmotic buffering agent. In step 6, essentially all of the cryoprotectant is removed. However, the osmotic buffering agent is retained. In step 7, the osmotic buffering agent is removed. Alternatively, steps 6 and 7 can be combined in a single step. That is, the osmotic buffering agent can be removed at the same time as the remainder of the cryoprotectant. In addition, if no osmotic buffering agent is used or if it is not removed, step 7 can be eliminated. Each of these concentration steps is maintained for a sufficient time to achieve approximate osmotic equilibration.

The temperature of the series of solutions is generally above −15° C., preferably between −15 and +15° C., and more preferably between 0° C. and +10° C. When step 1 is begun, the blood vessel is at a temperature above −75° C., preferably above −65° C. Thus, if the temperature of the blood vessel is below the temperature of the solution in which it is immersed in step 1, the blood vessel is further warmed to a temperature above -1 5C during step 1 of the cryoprotectant removal.

EXAMPLES

The external jugular vein was obtained from New Zealand white rabbits. The distal site of each vein segment above the bifurcation was cannulated in situ with a silicone tube. The proximal site was left open for fluid outflow. The vein segments, which were about 40–60 mm long, were perfused at 0° C. to 4° C.

Figure 1:
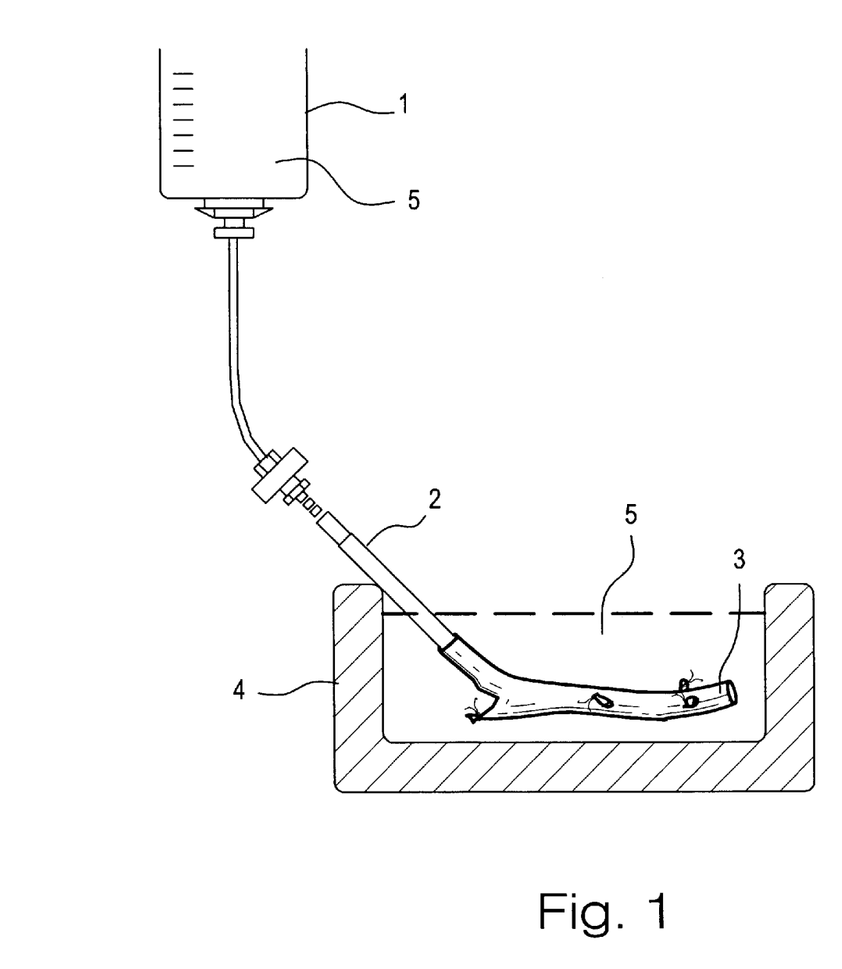
FIG. 1 shows an example of a perfusion system that can be used in the present invention.

To perfuse the veins, the perfusion system of FIG. 1 was used. The perfusion system comprises a reservoir 1 (a 60 CC syringe) containing perfusion solution 5 connected to the cannula 2 with a 3-way stopcock. The reservoir 1 was adjusted to physiologic pressure. The vein 3 was placed in a petri dish 4 (Dia.xH, 50×15 mm) containing perfusion solution 5. The perfusion solution 5 in both reservoir 1 and petri dish 4 was the same and was pre-cooled (0° C.–4° C.) and the petri dish 4 was placed in ice (0° C.–4° C.) during the perfusion process.

The vitrification solution used was VS55. The full strength VS55 solution was introduced in six serial steps. In the first step, the blood vessels were perfused with Euro-Collins solution, which is the carrier of VS55. In steps two to five, respectively, the amount of full strength VS55 in the solution was as follows: ⅛ VS55, ⅜ VS55; ⅝ VS55; and ⅞ VS55. In each case, the remainder of the solution was Euro-Collins solution. In the sixth step, the perfusion solution was full strength VS55. Exposure at each step was for 15 minutes.

Figure 2:
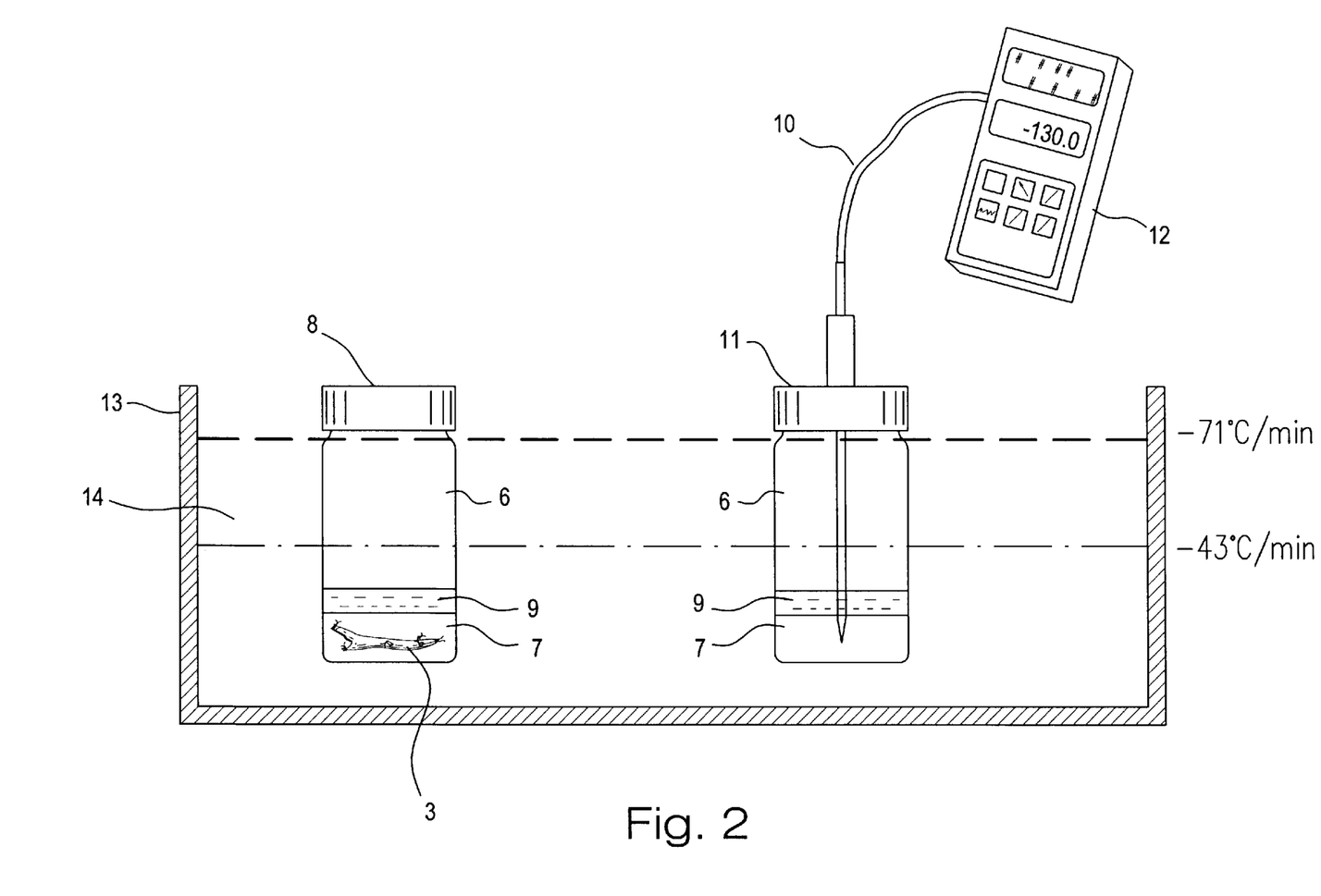
FIG. 2 shows a device that can be used for rapidly cooling the blood vessels.

After addition of the vitrification solution, the vein segments were rapidly cooled using the device demonstrated in FIG. 2. The vein segments 3, together with the silicone tube, were placed in a glass scintillation vial 6 (Dia.xH, 25×60 mm) containing 1 ml of pre-cooled full strength VS55 solution 7 to form the sample 8. The top of the vitrification solution 7 was covered with 0.7 ml of 2-methylbutane 9 (isopentane, freezing point: −160° C., density: 0.62) at 0° C. to 4° C. to prevent direct contact with air. A thermocouple 10 was inserted into a dummy sample 11 of the vitrification solution 7, and its output was monitored on a digital thermometer 12. Temperature was recorded throughout the cooling process.

Figure 3:
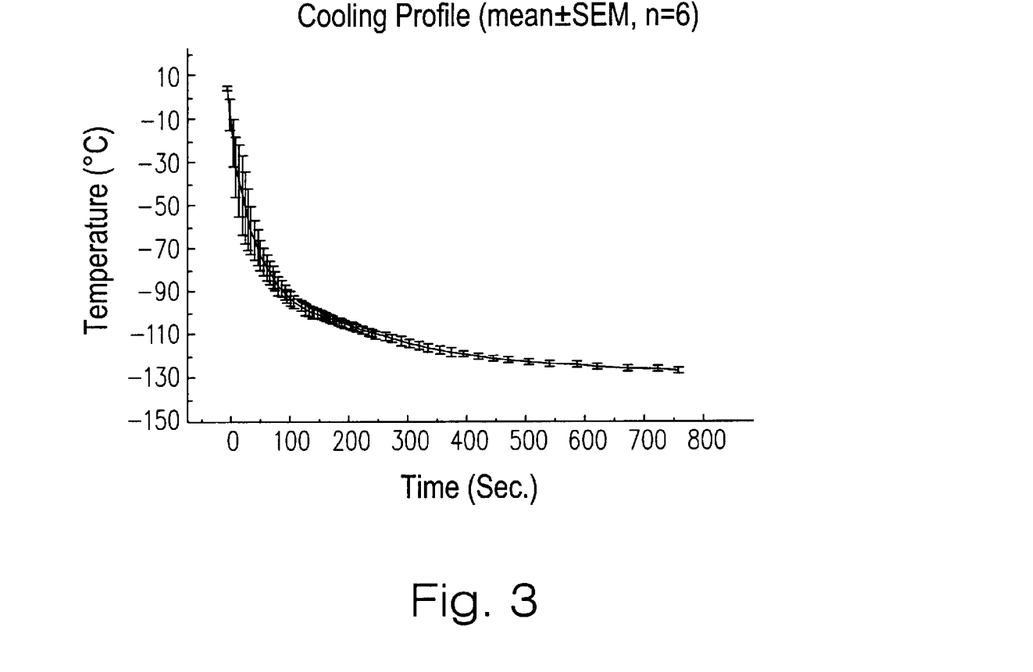
FIG. 3 shows the cooling profile generated by placing the glass scintillation vial 30 mm deep in precooled 2-methylbutane and then in cold air using the device of FIG. 2.

The cooling apparatus was set up inside a −135° C. freezer. The cooling rates were adjusted by placing the sample in a container 13 containing precooled 2-methylbutane 14. The cooling rates could be varied depending on the depth the vial was placed in 2-methylbutane (30 mm generate a cooling rate of 43° C./min; 60 mm generate cooling rate 71° C./min). By this technique, the samples were cooled rapidly (average rate =43±2° C./min) to −100° C. The samples were then slowly cooled (average rate =3±0.2° C./min) to −135° C. by taking the sample out of the container 13 of 2-methylbutane 14 and allowing the air in the −135° C. freezer to complete the cooling process. FIG. 3 shows the cooling profile using the technique of placing the glass scintillation vial 30 mm deep in precooled (−135° C.) 2-methylbutane. The sample was then stored in the −135° C. freezer for at least 24 hours.

Figure 4:
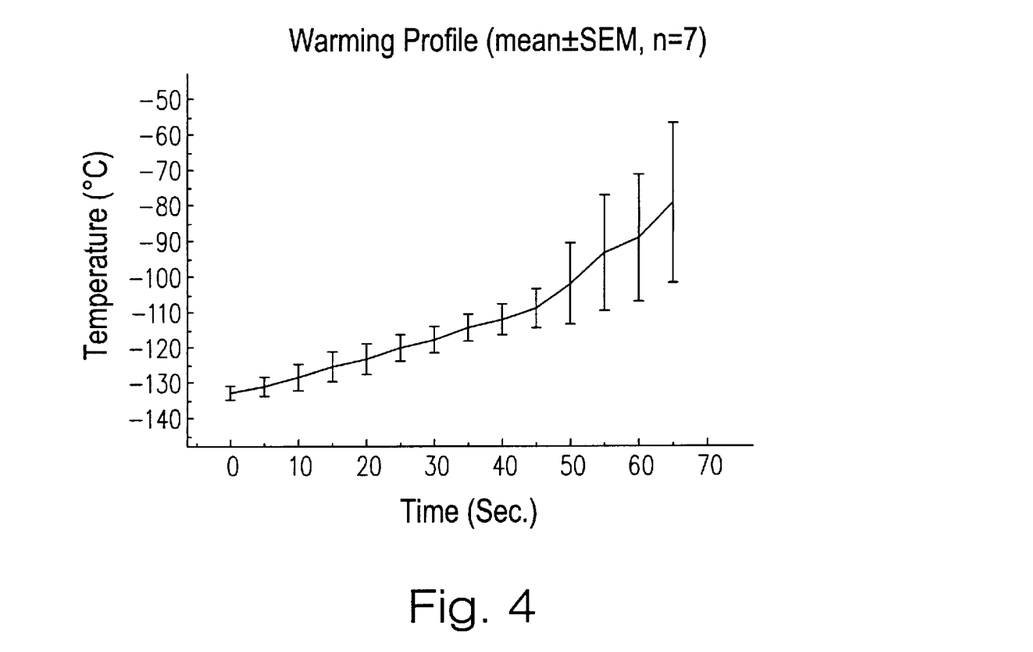
FIG. 4 shows the warming profile generated by placing the glass scintillation vial in cold air and then in a mixture of 30% DMSO/H$_2$O at room temperature.

After being stored for 24 hours, the veins were rewarmed in two stages, slow warming to −100° C. (average rate =30±2° C./min) and rapid warming to −65° C. (average rate =225±15° C./min). The slow warming rate was created by taking the sample to the top of the −135° C. freezer and the fast warming rate was generated by placing the glass vial in a mixture of 30% DMSO/$H_2O$ at room temperature. FIG. 4 shows the warming profile using this technique.

The VS55 vitrification solution was then removed in seven steps, using the perfusion system of FIG. 1. The perfusion solution 5 in both reservoir 1 and petri dish 4 was the same and was pre-cooled (0° C.–4° C.) and the petri dish 4 was placed in ice (0° C. to 4° C.) during the perfusion process. Thus, during the first step the blood vessel is further warmed to a temperature between 0° C. and 4° C.

In all of the steps except the last step, the solution contained, in addition to the cryoprotectant solution, 400 to 200 mM mannitol. In steps one to five, the amount of full strength VS55 in the solution was as follows: 4/8 VS55; 3/8 VS55; 2/8 VS55; 1/8 VS55; and 0.5/8 VS55, with the remainder of the solution being a mannitol-containing Euro-Collins solution (The 4/8 strength VS55 solution contained 400 mM mannitol and the cryoprotectant-free Euro-Collins solution that was mixed therewith to form the lower cryoprotectant concentration solutions contained 200 mM mannitol. Thus, as the amount of VS55 was decreased, the amount of mannitol was decreased between 400 and 200 mM.) In step six, Euro-Collins solution containing 200 mM mannitol was used. In step 7, a Euro-Collins solution that did not contain mannitol was used. Exposure at each step was for 15 minutes.

Figure 5:
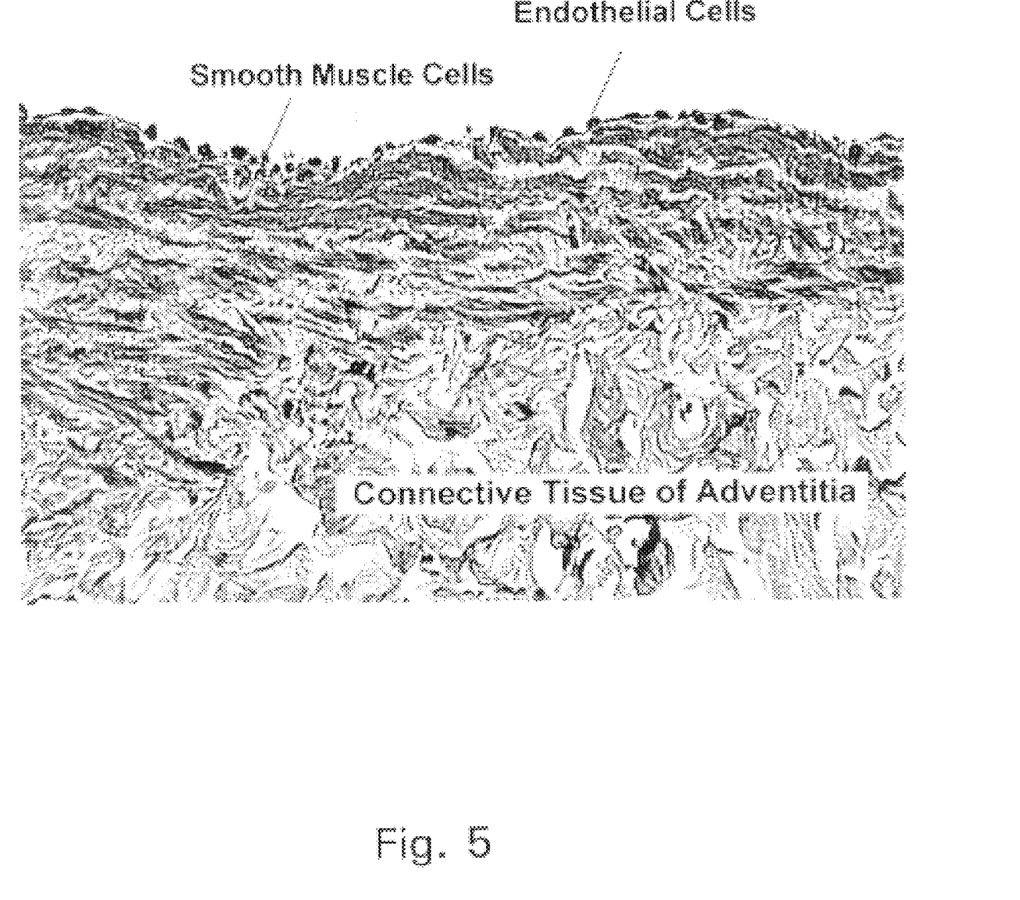
FIG. 5 shows the structural integrity of vein segments following preservation by vitrification.

The morphology studies showed that the structural integrity of vein segments was preserved following vitrification. FIG. 5 demonstrates a histological section of a vitrified rabbit jugular vein showing intact morphological features, including endothelial cells, smooth muscle and the connective tissue of the adventitia.

Vein graft implantation experiments demonstrate the viability of the vein segments after vitrification as compared to fresh autologous veins into the carotid position as a control procedure. New Zealand white rabbits (average weight 2.0 to 2.5 kg) underwent a right common carotid interposition bypass graft. The fresh, or vitrified, reversed ipsilateral external jugular veins were used as syngeneic grafts. Animals were sacrificed at either two or four weeks after implantation. Vein grafts were harvested for histology studies.

Operative Procedure:

Anesthesia was induced in New Zealand white rabbits with an injection of a mixture of ketamine hydrochloride (60 mg/kg) and xylazine (6 mg/kg) and maintained in intubated animals using isoflurane delivered in oxygen. A single-dose antibiotic prophylaxis in the form of enrofloxacin (5 mg/kg) was given intramuscularly at the time of induction. The operation was performed with an operating microscope under sterile conditions. After exposure through a right longitudinal neck incision, the right external jugular vein was identified; its branches were cauterized and then removed. Fresh veins were implanted immediately. Vitrified veins were rewarmed in the laboratory and transported to the operation room in DMEM medium on ice.

Figure 6:
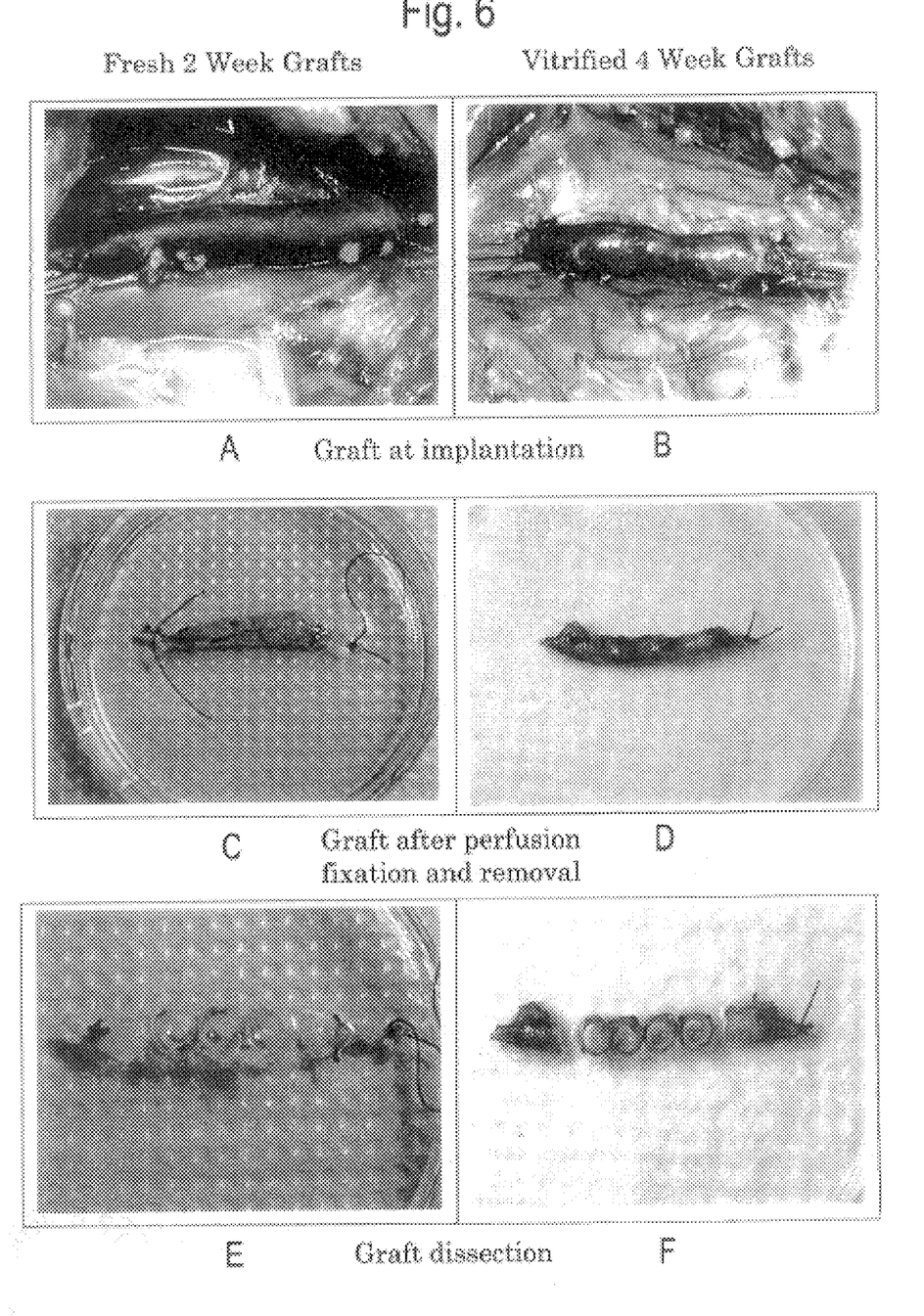
FIGS. 6A–F show the fresh and vitrified grafts at implantation, after perfusion, fixation and removal, and after graft dissection.

At the time of implantation, the right common carotid artery was identified and dissected. Heparin (200 IU/kg) was administered intravenously. A proximal longitudinal arteriotomy was made, and one end of the reversed jugular vein was anastomosed to the artery end-to-side with a continuous 8–0 microvascular prolene suture. The distal anastomosis was performed similarly (FIG. 6, A–B). Throughout the procedure, care was taken to avoid unnecessary instrumentation of the vein graft. The right common carotid was ligated and divided between the two anastomoses with 4–0 silk ligatures. Hemostasis was achieved, and the wound was subsequently closed in layers.

During recovery, analgesic (buprenorphine 0.05 mg/kg, S.C.) was provided as necessary. Animals were observed daily for signs of infection, illness, injury, or abnormal behavior. Sick or injured animals were referred immediately for veterinary care or euthanized. At the time of graft harvest, under the same anesthetic regimen described above, the original incision was reopened and both the vein grafts and the non-operated contralateral veins were isolated. Following heparinisation, the vein grafts and contralateral controls were perfusion fixed in situ at 80 mm Hg (FIG. 6, C–D). Grafts were perfused with a standardized initial infusion of lactated Ringer's solution followed by 2% glutaraldehyde made up in 0.1M cacodylate buffer supplemented with 0.1M sucrose to give an osmolality of approximately 300 mOsm/kg. After immersion in fixative for 24–48 hours, the graft was divided into a proximal, middle and distal parts (FIG. 6, E–F). Cross-sections from the central region and longitudinal-sections from proximal and distal anastomosis regions were taken for histology studies.

Graft Patency:

Using these techniques, 10 fresh grafts have been harvested, and 9 grafts were patent two or four weeks post-operatively. One four-week graft that was not patent was not attributable to technical complications. In this study, we achieved similar patency results to those obtained by other investigators using the same surgical procedures. In addition, 12 vitrified grafts were harvested, and 11 grafts remained patent. The failed graft was found at the time of harvest. It was due to a surgical error made in the proximal anastomosis that blocked blood flow. This study demonstrated similar patency rates in fresh and vitrified autologous vein grafts. The study also included one allograft vein segment that was patent 2-weeks after explantation.

Figure 7:
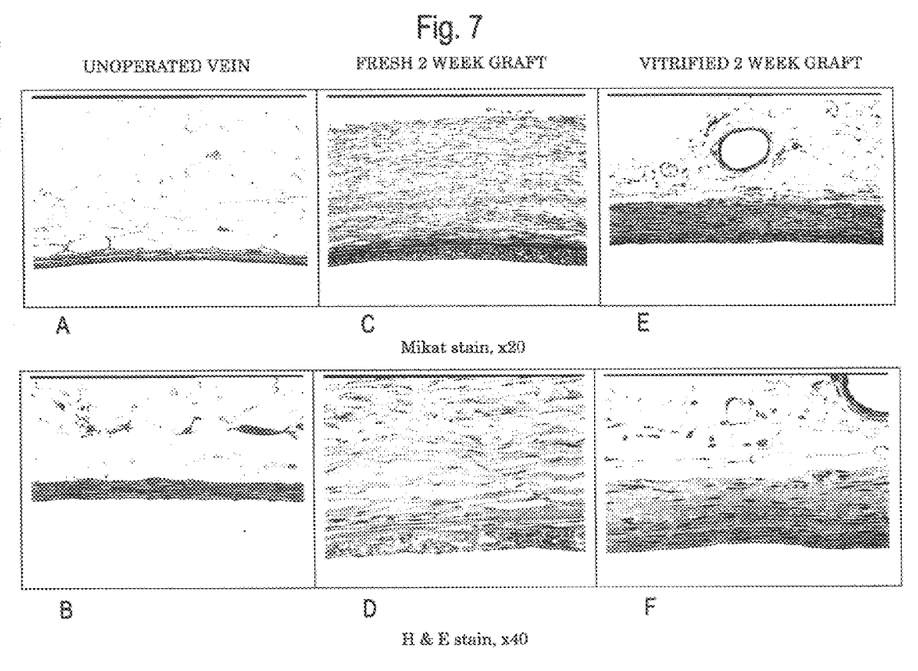
FIGS. 7A–F show the morphology of non-operated veins, fresh vein grafts and vitrified vein grafts in Mikat or H&E staining.

Histology Study:

FIG. 7 shows the morphology of non-operated veins, fresh vein grafts and vitrified vein grafts in Mikat or H&E staining. Non-operated control veins showed unaltered endothelial cells on the intimal surface and their walls were composed of a couple of layers of smooth muscle cells (FIG. 7, A–B). At 2 weeks post-transplant, a smooth muscle cell proliferative lesion-intimal hyperplasia and a thickened media appeared in fresh vein grafts (FIG. 7, C–D). Similarly, the vitrified veins developed an intimal hyperplasia layer, which is however, much thinner than fresh vein grafts (FIG. 7, E–F). This study demonstrated that intimal hyperplasia has been reduced in vein grafts pretreated by vitrification. This reduced intimal hyperplasia was a particularly unexpected discovery.

Physiology Study:

Vein rings, which are about 4 mm long segments of rabbit external jugular veins, are vitrified in VS55 by the method described above for longer external jugular vein segments, except that perfusion is not used. After being rewarmed, the vein rings are mounted between two stainless steel wire hooks and suspended in a vascular smooth muscle bath containing 5 ml of Krebs Henseleit (KH) solution, which is gassed continuously with 95% $O_2$ and 5% $CO_2$ at 37° C. The baseline tension of all vein rings is adjusted to 0.25 to 0.75 g. Changes in tension are recorded by force transducers. After 1 hour of equilibration, the vein rings are pretested with potassium chloride for contraction. After rinsing with KH solution, the vein rings are equilibrated for another 30 minutes prior to the start of experiment. During a relaxation experiment, contraction of the vein rings is produced by $10^{-6}$M norepinephrine and, after the contractile response plateaus, cumulative concentrations of acetylcholine ($10^{-10}$M to $10^{-4}$M) are added to the bathing medium to induce the endothelium dependent relaxation response.

In the current study, histamine, bradykinin, angiotensin II, and norepinephrine are tested in rabbit jugular vein ring segments vitrified with VS55 and fresh vein rings. Both histamine and bradykinin produce contraction in the vein via their local receptors. Norepinephrine acts directly on the adrenoceptor, while angiotensin II binds to AT receptors and acts through local renin-angiotensin systems.

Table 4 below demonstrates that the vitrified vein rings produce similar contractile function as compared to fresh vein rings.

TABLE 4

Maximal Physiological Responses*

|  | Control (g) | Vitrified (g) | % |
|---|---|---|---|
| Histamine | 1.78 ± 0.19 | 1.55 ± 0.27 | 87.1 |
| Bradykinin | 1.75 ± 0.18 | 1.49 ± 0.15 | 85.1 |
| Angiotensin II | 0.58 ± 0.06 | 0.49 ± 0.09 | 84.5 |
| Norepinephrine | 0.99 ± 0.12 | 0.83 ± 0.14 | 83.8 |

*Values expressed as the Mean (± SEM).
Vitrified vein rings vitrified with vitrification solution VS55 (n = 26).
Control = fresh vein rings (n = 15).
% = percent of corresponding fresh controls.

Artery rings are vitrified in VS55 by the method described above for vein rings. After being rewarmed, norepinephrine and phenylephrine are tested in artery ring segments vitrified with VS55 and fresh artery rings.

Table 5 below demonstrates that the vitrified artery rings produce similar contractile function as compared to fresh artery rings.

TABLE 5

Maximal Physiological Responses*

|  | Control (g) | Vitrified (g) | % |
|---|---|---|---|
| Norepinephrine | 2.84 ± 0.38 | 2.58 ± 0.23 | 90.8 |
| Phenylephrine | 2.53 ± 0.45 | 2.23 ± 0.29 | 88.3 |

*Values expressed as the Mean (± SEM).
Vitrified artery rings vitrified with vitrification solution VS55 (norepinephrine n = 37, phenylephrine n = 23).
Control = fresh vein rings (norepinephrine n = 16, phenylephrine n = 12).
% = percent of corresponding fresh controls.

What is claimed is:

1. A method for vitrification of a blood vessel, comprising:
   immersing the blood vessel in a series of solutions having increasing concentrations of cryoprotectant to achieve a cryoprotectant concentration sufficient for vitrification, each solution of said series of solutions having a temperature above −15° C.;
   cooling the blood vessel in a solution having said cryoprotectant concentration sufficient for vitrification at an average rate of from 30 to 60° C. per minute from a temperature above −15° C. to a temperature between −80° C. and the glass transition temperature; and
   further cooling the blood vessel at an average rate less than 10° C. per minute from a temperature that is between −80° C. and the glass transition temperature to a temperature below the glass transition temperature to vitrify the blood vessel.

2. The method of claim 1, wherein the immersion step comprises:
   (a) immersing the blood vessel with a cryoprotectant-free solution;
   (b) immersing the blood vessel with at least one solution containing cryoprotectant at a concentration less than said concentration sufficient for the vitrification; and
   (c) immersing the blood vessel with a solution containing cryoprotectant at said concentration sufficient for vitrification.

3. The method of claim 2, wherein the blood vessel is also perfused with the solution in each of steps (a)–(c).

4. The method of claim 2, wherein, in each of steps (a)–(c), the blood vessel is immersed in the solution for a sufficient time to achieve approximate osmotic equilibration.

5. The method of claim 2, wherein, in each of steps (a)–(c), the blood vessel is immersed in the solution for at least 10 minutes.

6. The method of claim 2, wherein step (b) comprises immersing the blood vessel in a series of four solutions having increasing concentrations of cryoprotectant, each of which has a cryoprotectant concentration less than said concentration sufficient for vitrification.

7. The method of claim 6, wherein the blood vessel is immersed in each solution of said series of four solutions for a sufficient time to achieve approximate osmotic equilibration.

8. The method of claim 6, wherein the blood vessel is immersed in each solution of said series of four solutions for at least 10 minutes.

9. The method of claim 6, said four increasing concentrations being 5 to 20% of said cryoprotectant concentration sufficient for vitrification; 15 to 35% of said cryoprotectant concentration sufficient for vitrification; 40 to 60% of said cryoprotectant concentration sufficient for vitrification; and 65 to 85% of said cryoprotectant concentration sufficient for vitrification.

10. The method of claim 1, wherein said cryoprotectant concentration sufficient for vitrification is between 6 and 9.5M.

11. The method of claim 1, wherein said cryoprotectant solution comprises dimethyl sulfoxide, formamide, and 1,2-propanediol.

12. The method of claim 11, wherein said cryoprotectant solution comprises 20–30% w/v dimethyl sulfoxide, 10–20% w/v formamide and 10–20% w/v 1,2-propanediol.

13. A method for vitrification of a blood vessel and subsequent removal from vitrification, comprising:
   immersing the blood vessel in a series of solutions having increasing concentrations of cryoprotectant to achieve a cryoprotectant concentration sufficient for vitrification, each solution of said series of solutions having a temperature above −15° C.;
   cooling the blood vessel in a solution having said cryoprotectant concentration sufficient for vitrification at an average rate of from 30 to 60° C. per minute from a temperature above −15° C. to a temperature between −80° C. and the glass transition temperature;

further cooling the blood vessel at an average rate less than 10° C. per minute from a temperature that is between −80° C. and the glass transition temperature to a temperature below the glass transition temperature to vitrify the blood vessel;

warming the vitrified blood vessel at an average rate of from 20 to 40° C. per minute to a temperature between −80° C. and the glass transition temperature;

further warming the blood vessel at an average rate of 200 to 300° C. per minute to a temperature above −75° C.; and immersing the blood vessel in a series of solutions having decreasing concentrations of cryoprotectant to obtain a blood vessel in a cryoprotectant-free solution.

14. The method of claim 13, wherein at least 70% of smooth muscle function and graft patency rate of the blood vessels are maintained as compared to fresh blood vessels.

15. The method of claim 13, wherein said method provides for reduced intimal hyperplasia in said blood vessel as compared to fresh blood vessels.

* * * * *